(12) United States Patent
Béland et al.

(10) Patent No.: US 6,443,959 B1
(45) Date of Patent: Sep. 3, 2002

(54) SURGICAL EXTRACTOR

(75) Inventors: Pascal Béland, Drummondville; Germain Béland, Sherbrooke; Jacques Poisson, Fleurimont, all of (CA)

(73) Assignee: Instruments Medicaux GB Inc., Sherbrook (CA)

( * ) Notice: Subject to any disclaimer, the term of this patent is extended or adjusted under 35 U.S.C. 154(b) by 0 days.

(21) Appl. No.: 09/503,923

(22) Filed: Feb. 14, 2000

(30) Foreign Application Priority Data

Feb. 16, 1999 (CA) ............................................. 2261192

(51) Int. Cl.$^7$ ............................................. A61B 17/22
(52) U.S. Cl. .......................................................... 606/127
(58) Field of Search ............................ 606/1, 191, 198, 606/159, 170, 171, 180, 114, 127, 128, 113, 110, 115; 600/201–211, 214, 215, 219; 604/105, 106

(56) References Cited

U.S. PATENT DOCUMENTS

| 3,320,957 | A | * | 5/1967 | Sokolik ........................ 606/170 |
| 3,495,586 | A | * | 2/1970 | Regenbogen ................ 606/198 |
| 4,347,846 | A | | 9/1982 | Dormia |
| 4,807,626 | A | | 2/1989 | McGirr |
| 4,927,427 | A | * | 5/1990 | Kriauciunas et al. ....... 606/128 |
| 5,064,428 | A | | 11/1991 | Cope et al. |
| 5,147,371 | A | | 9/1992 | Washington et al. |
| 5,275,610 | A | | 1/1994 | Eberbach |
| 5,339,803 | A | | 8/1994 | Mayzels et al. |
| 5,368,597 | A | | 11/1994 | Pagedas |
| 5,454,365 | A | * | 10/1995 | Bonutti ........................ 600/205 |
| 5,569,284 | A | * | 10/1996 | Young et al. ................ 606/170 |
| 5,611,803 | A | | 3/1997 | Heaven et al. |
| 5,656,012 | A | | 8/1997 | Sienkiewicz |
| 5,678,572 | A | * | 10/1997 | Shaw et al. ................. 606/198 |
| 5,681,280 | A | * | 10/1997 | Rusk et al. .................. 604/105 |
| 5,702,365 | A | * | 12/1997 | King ............................ 604/105 |
| 5,730,726 | A | | 3/1998 | Klingenstein |
| 5,782,839 | A | | 7/1998 | Hart et al. |
| 5,788,709 | A | | 8/1998 | Riek et al. |
| 5,788,710 | A | * | 8/1998 | Bates et al. ................. 606/113 |
| 6,193,730 | B1 | | 2/2001 | Béland |
| 2001/0031981 | A1 | * | 10/2001 | Evans et al. ................ 606/200 |

FOREIGN PATENT DOCUMENTS

| DE | 42 16 165 | 11/1992 |
| EP | 0 512 729 | 4/1992 |
| WO | 98/19608 | 5/1998 |

* cited by examiner

Primary Examiner—Michael J. Milano
Assistant Examiner—Vy Q. Bui
(74) Attorney, Agent, or Firm—Collard & Roe, P.C.

(57) ABSTRACT

A surgical extractor for use in laparascopy. It has a first hollow tube called "slide" and a second hollow tube called "pusher", which is mounted in a sliding manner over the slide. The slide has a first open end, a second end and a long radial opening close to the second end. A set of flexible rods called "straps" extend in line with the pusher. Each strap has a first end fixed in a rigid manner to the pusher and a second end connected in a rigid manner to the slide close to the second end of the same. Handles are provided for applying a pressure onto the pusher so as to move it over a given stroke distance from a rest position to an opening position closer to the second end of the slide, such causing the straps to fold up and open like petals over the radial opening and thus to allow grasping in a radial direction of an organ to be extracted from the body of the patient. The same handles are also used to bring the pusher back from its opening position to its rest position while forcing, if needs be, the straps to unfold and thus crush the organ grasped by them, such permitting to the organ to pass inside the slide and thus to be extracted from the same through the first open end thereof.

14 Claims, 8 Drawing Sheets

SURGICAL EXTRACTOR

TECHNICAL FIELD OF THE INVENTION

The present invention relates to an apparatus hereinafter called "surgical extractor" which is intended to be used in surgery, and more specifically in laparoscopy, to extract the gall-bladder or any other organ or element of a non-negligible size from the body of a patient during an operation.

BRIEF DESCRIPTION OF THE PRIOR ART

There are numerous patents disclosing surgical extractors, which are devised to remove stones, tissues or other elements from the body of a patient. By way of examples, reference can be made to the following U.S. patents:

U.S. Pat. No. 4,807,626 (1989) McGIRR
U.S. Pat. No. 5,147,371 (1992) WASHINGTON
U.S. Pat. No. 5,788,709 (1998) RIEK et al

Some of these known extractors are specially adapted for a percutaneous use in vascular organs such as the lever or the kidneys, or in laparoscopy (see the WASHINGTON and RIEK et al patents).

There are also patents disclosing extractors that are medical but not surgical. By way of non-restrictive example of such patents, reference can be made to the following U.S. patent which discloses an extractor devised for removing faecal imprecations from the rectum of a patient:

U.S. Pat. No. 5,730,726 (1998) KLINGENSTEIN

There are furthermore numerous patents disclosing apparatuses known as "surgical retractors", which are used for separating or spacing away part of an organ or of the body of a patient during a surgery, especially a laparoscopy. By way of non-restrictive examples of such patents, reference can be made to the following U.S. patents:

U.S. Pat. No. 5,275,610 (1994) EBERBACH
U.S. Pat. No. 5,339,803 (1994) MAYZELS et al
U.S. Pat. No. 5,656,012 (1997) SIENKIEWICZ

If all these patents disclose apparatuses having a structure and a utility that may a priori be considered as similar to those of the extractor according to the invention, none of them discloses a surgical extractor especially devised for use in laparoscopy, which, thanks to its structure, is devised:

1—to open on one side only of its longitudinal axis, in order to grasp and catch with more precision the organ to be extracted; and 2—to apply a substantial compression force onto the organ to be extracted after it has been grasped in order to crush it, grind it, if needs be, and thus reduce its size; and 3—to have an open internal tube that gives access not only to the extraction zone but also to the organ that is grasped in order to dissect it and suck it in.

SUMMARY OF THE INVENTION

Thus, the object to the invention is a device hereinafter called "surgical extractor", which is intended to be used for extracting an organ from the body of a patient during an operation and which, thanks to its structure, satisfies the three needs listed hereinabove, thereby making it useful in particular in laparoscopy for extracting, through a tube of restricted diameter (one centimeter or less), organs that are of a not negligible size and, in fact, much larger than those of stones or tissues. By way of non-limitative example of such an organ of non-negligible size, reference can be made to the gallbladder.

The surgical extractor according to the invention is characterized in that it comprises:

a first hollow tube hereinafter called "slide", said slide having a rectilinear longitudinal axis and a constant cross-section, a first open end and a second end, and a long radial opening close to the second end, said radial opening extending over more than half of the section of the slide; and a second hollow tube hereinafter called "pusher", which is mounted in a sliding manner over the slide.

Several flexible rods hereinafter called "straps" extend in line with the pusher. Each of the straps has a first end fixed in a rigid manner to the pusher and a second end connected in a rigid manner to the slide close to the second end of the same. These straps are distributed to extend over the radial opening of the slide.

Means are also provided for applying a pressure onto the pusher so as to:

in a first step, move the pusher over a given stroke distance from a rest position to an opening position closer to the second end of the slide, such causing the straps to fold up and open like petals over the radial opening and thus to allow grasping in a radial direction of an organ to be extracted from the body of the patient; and in a second step, bring the pusher back from its opening position to its rest position while forcing, if needs be, the straps to unfold and thus crush the organ grasped by them, such permitting to the organ to pass inside the slide and thus to be extracted from the same through the first open end thereof.

The above mentioned means for applying a pressure onto the pusher preferably consist of handles respectively fixed to the slide and the pusher close to the first open end. By moving the handle of the pusher away from the one of the slide, one may move the pusher in the opening position. It is worth noting that the straps, due to their positioning, fold up above the opening and thus can be oriented in the radial direction mentioned hereinabove to allow directional grasping of the organ to be extracted. After such grasping, by moving the handles toward each other while pressing on them if needs be, one may move the pusher back in the rest position while crushing the organ grasped by the straps. If the crushing that is carried out is not sufficient to allow extraction of the organ, one may insert a knife through the slide because it is hollowed and opened at its first end, and thus one may cut or grind the organ in smaller parts that are capable of being extracted through the slide.

According to a preferred embodiment of the invention, the surgical extractor may incorporate a drill extending over the full length of the slide within the same for crushing and extracting the grasped organ. This bit may be driven in rotation by a motor located close to the first open end of the slide, If needs be, a radial outlet may be provided close to the first open end of the slide, in order to connect it to a vacuum suction device.

In accordance with another preferred embodiment of the invention, a bag called "sealing bag" provided of a radial slot, can be mounted onto the slide and straps in order to cover at least the radial opening and the second end of the slide. The slot of the bag is located so as to extend above the opening. When the pusher is moved in the opening position, the straps while they fold up, cause the slot to open and thus allow grasping of the organ that is then inserted within the bag. When the pusher is moved in the rest position, the bag is retracted together with the straps and avoids that the organ or crushed parts of it escape within the body of the patient.

Advantageously, a ring can be mounted in a sliding manner onto the pusher to maintain the sealing bag and permit to the operator to slide it in one way or the other depending on what is needed.

The invention and its advantages will be better understood upon reading the following non-limitative description that follows of several preferred embodiments thereof, mainly with reference to the accompanying drawings.

Figure 1:
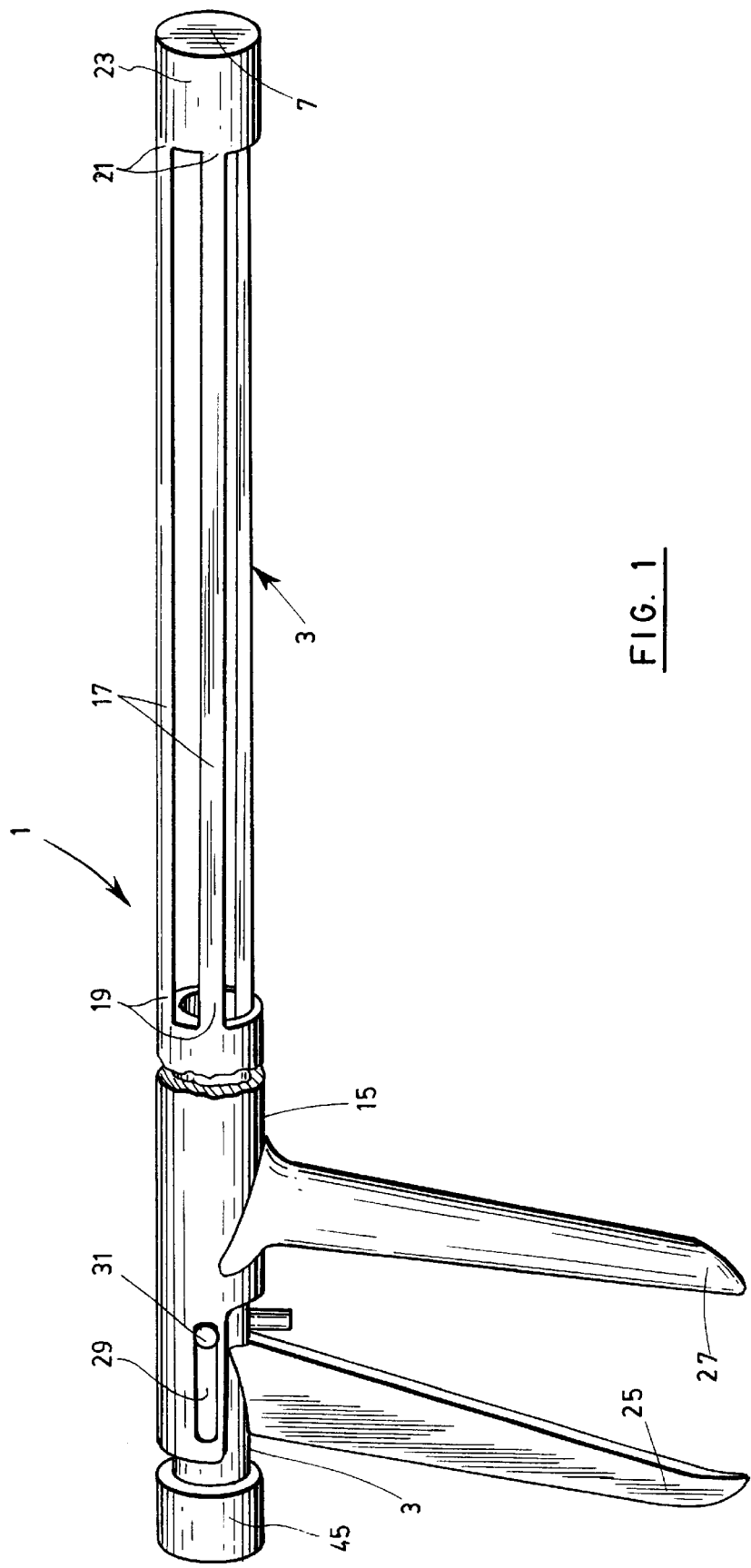
FIG. 1 is a perspective view of a surgical extractor according to a first embodiment of the invention, said extractor being illustrated in closed position, which is the position that is used for the introduction of the extractor within the body of a patient and during its removal after a use.
Figure 2:
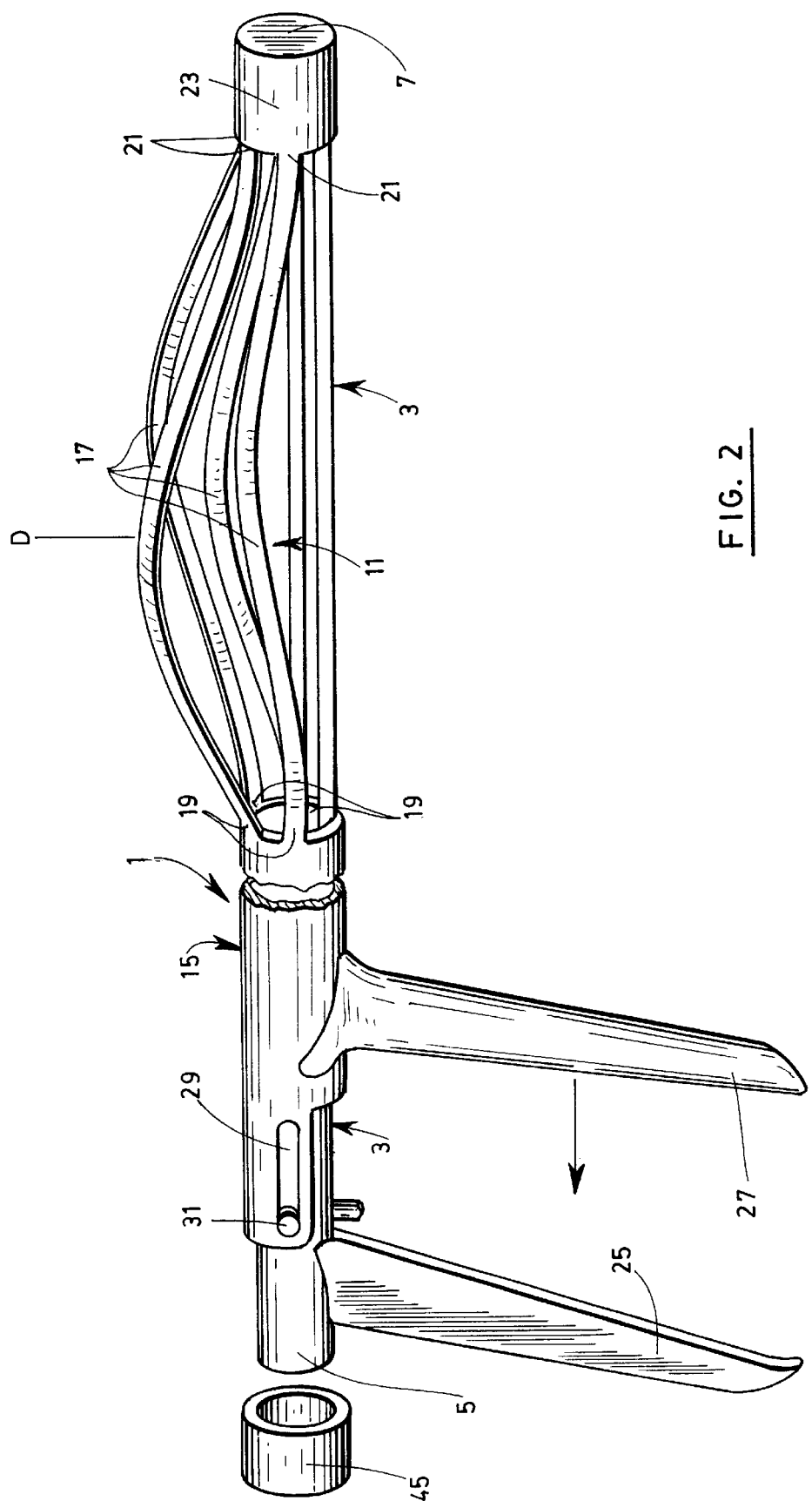
FIG. 2 is a view similar to FIG. 1, showing the extractor in open position, when it is ready to extract an organ.
Figure 3:
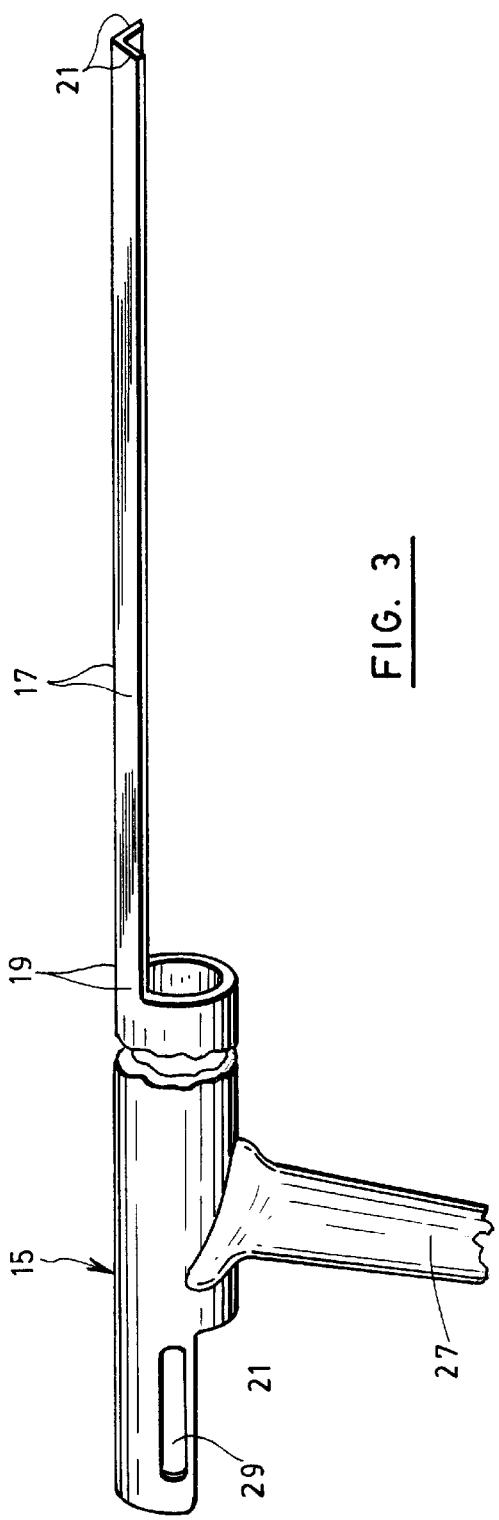
FIG. 3 is a perspective view of the pusher of the extractor shown in FIGS. 1 and 2.
Figure 4:
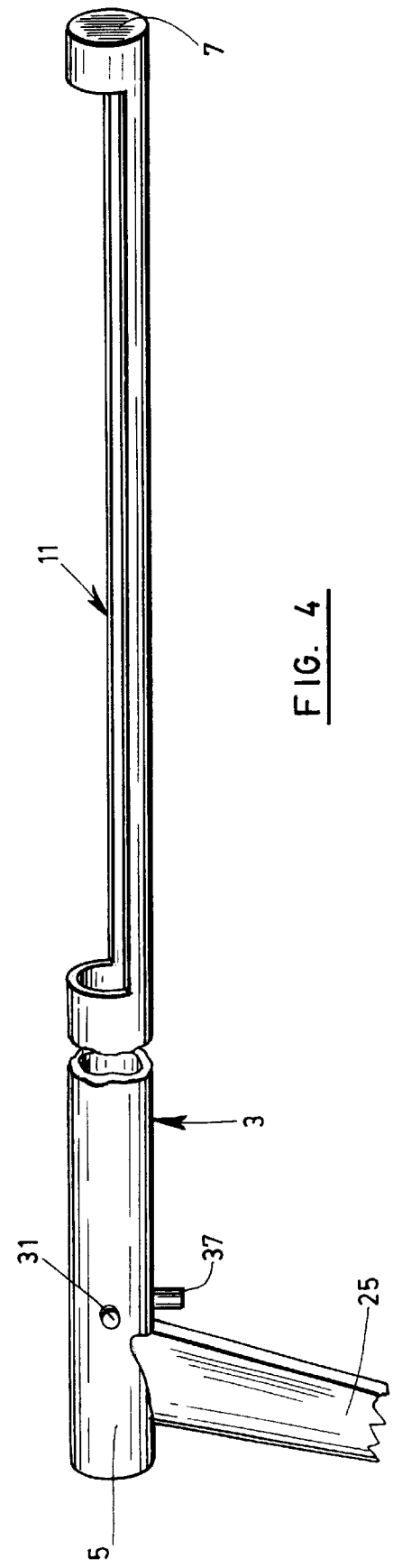
FIG. 4 is a perspective view of the slide of the extractor shown in FIGS. 1 and 2.

It is worth mentioning that the proportions used in drawings are not actually representative of the real dimensions of the illustrated surgical extractors. These proportions were used only for the purpose of making the drawings clearer. To evaluate the real dimensions of the extractors according to the invention, the reader is kindly requested to refer to what is indicated in the following description. It is worth mentioning also that, in the drawings, the same reference numerals have been used to identify the same structural elements, whatever be the illustrated embodiment.

DESCRIPTION OF SEVERAL PREFERRED EMBODIMENTS OF THE INVENTION

The surgical extractor 1 according to the invention as shown in the accompanying drawings comprises two basic structural components.

The first one of these components is a first hollow tube 3 hereinafter called "slide", which is made of a metal or a rigid plastic material that is biocompatible. The slide 3 has a rectilinear longitudinal axis and a constant cross-section. It also has a first open end 5 and a second end 7 which may be open or closed, as wanted. In the embodiment shown in FIGS. 1 to 7, this second end 7 is closed. In the illustrated embodiments shown in FIGS. 8 to 10, it is open. The slide 3 further has a long radial opening 11 close to the second end 7, which extends over more than half of the section of the slide 3.

Advantageously, the slide 3 has a length ranging from 40 to 50 cm and a diameter lower than 2 cm. This diameter is preferably of about 1 cm. The radial opening then has a length comprised between 15 and 25 cm. This radial opening is preferably 20 cm long.

The second basic structural component of the extractor 1 is another hollow tube 15 hereinafter called "pusher", which is shaped and sized to be mounted in a sliding manner over the slide 3. The pusher 15 is also made of a biocompatible metal or plastic material.

Several flexible rods hereinafter called "straps", extend in line with the pusher. Each of the straps has a first end 19 fixed in a rigid manner to the pusher 15 and a second end 21 connected in a rigid manner to the slide 3 close to the second end 7 thereof. These straps 17, are distributed over the radial opening 11 of the slide 3. Their number may vary depending on the operators need (see, by way of comparison, FIGS. 2 and 5).

As shown in all the figures, the straps preferably form an integral part of the pusher. Their second ends 21 may be welded directly to the second end 7 of the slide (see FIGS. 3 to 5) or be integral to a ring 23 which is rigidly fixed to the second end of the slide (see FIGS. 1 and 2).

According to an important feature of the invention, means are provided for applying a pressure onto the pusher so as to:

in a first step, move the pusher 15 over a given stroke distance of about 4 to 8 cm (preferably 5.5 cm) from a rest position (see FIG. 1) to an opening position (see FIGS. 2 and 5) closer to the second end of the slide, such causing the straps to fold up and open like pedals over the radial opening and thus allowing grasping in a given radial direction "D" of an organ to be extracted from the body of a patient; and in a second step, bring the pusher 15 back to from its opening position (see FIGS. 2 and 5) to the rest position (see FIG. 1) while forcing, if needs be, the straps 17 to unfold and thus crush the organ grasped by them, such permitting to the organ to pass inside the slide 3 and to be extracted through the first open end 5 thereof.

In the illustrated embodiments, said means for applying a pressure onto the pusher preferably consist of handles 25, 27 respectively fixed to the slide 3 and pusher 15 close to the first open end of the slide. By moving the handle 27 of the pusher 15 away from the one 25 of the slide 3, one may move the pusher 15 in the opening position. It is worth noting here that the straps 17, due to their positioning, fold up above the radial opening and thus can be oriented in the axial direction "D" to allow directional grasping of the organ to be extracted. After such a grasping, by moving the handles 25, 27 toward each other while pressing on them if needs be, one may move the pusher 15 back in the rest position while crushing the organ grasped by the straps 17. If the crushing that is carried out is not sufficient to allow extraction of the organ, one may insert a knife (not shown) through the slide since it is hollow and opened at its first end, and thus cut or grind the organ in smaller parts that are capable of being extracted through the slide 5.

To allow an efficient axial movement of the pusher 15 over the slide 3, a guiding system may be provided. This system preferably consists of at least one axial slot 29 made in the pusher and in which is inserted a guiding flange 31 projecting radially from the external surface of the slide 3.

Figure 5:
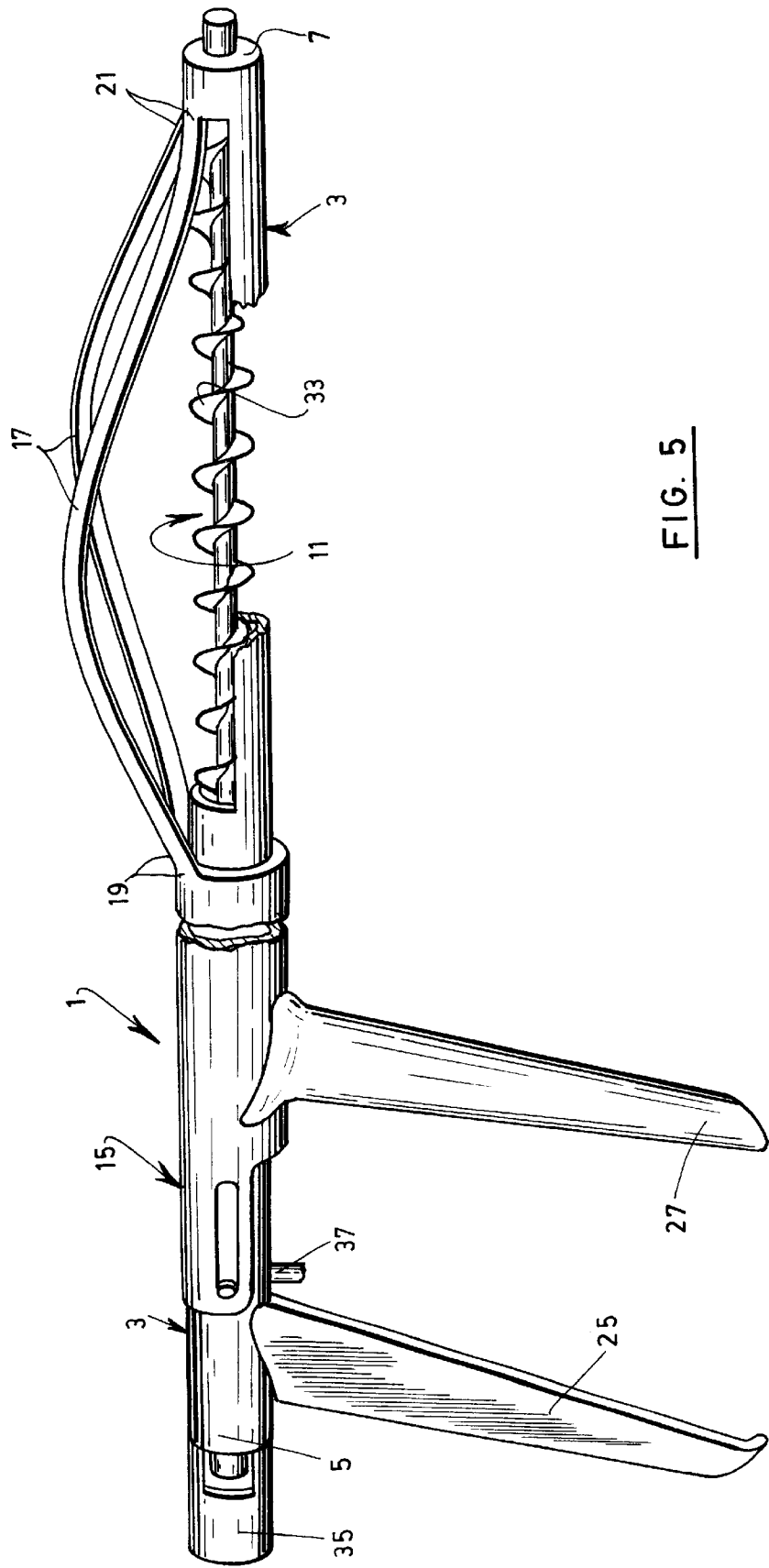
FIG. 5 is a perspective view of a surgical extractor according to a second embodiment of the invention, said extractor being shown in open position and provided with a drill and a motor for facilitating extraction of the organ to be extracted.

In the preferred embodiment shown in FIG. 5, the surgical extractor 1 may incorporate a drill 33 extending over the full length of the slide 3 within the same, in order to crush and extract the grasped organ. The drill 33 is driven into rotation by a motor 35 located close to the first open end 5 of the slide.

If needs be, a supplemental radial outlet 37 (see FIGS. 4 and 5) can be provided at the first open end 1 of the slide 3, for connection thereof to a vacuum suction device.

Figure 6:
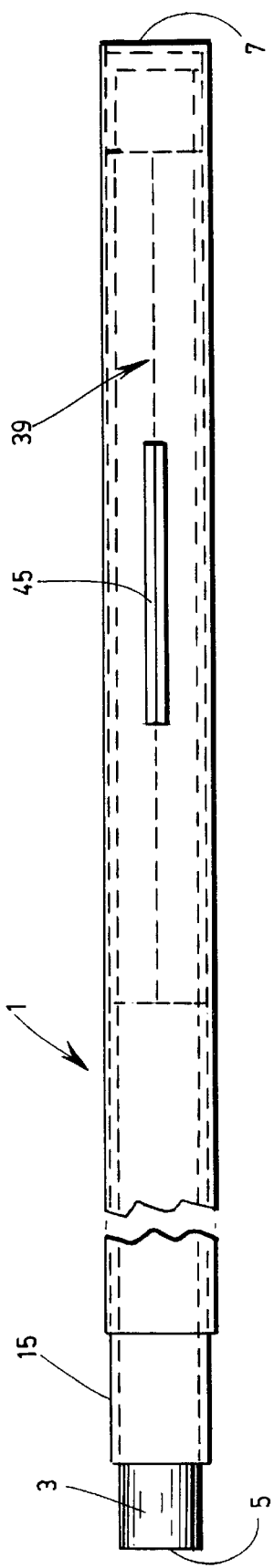
FIGS. 6 and 7 are top plan views in open and closed position of the head of a surgical extractor according to the invention, provided with a sealing bag.
Figure 7:
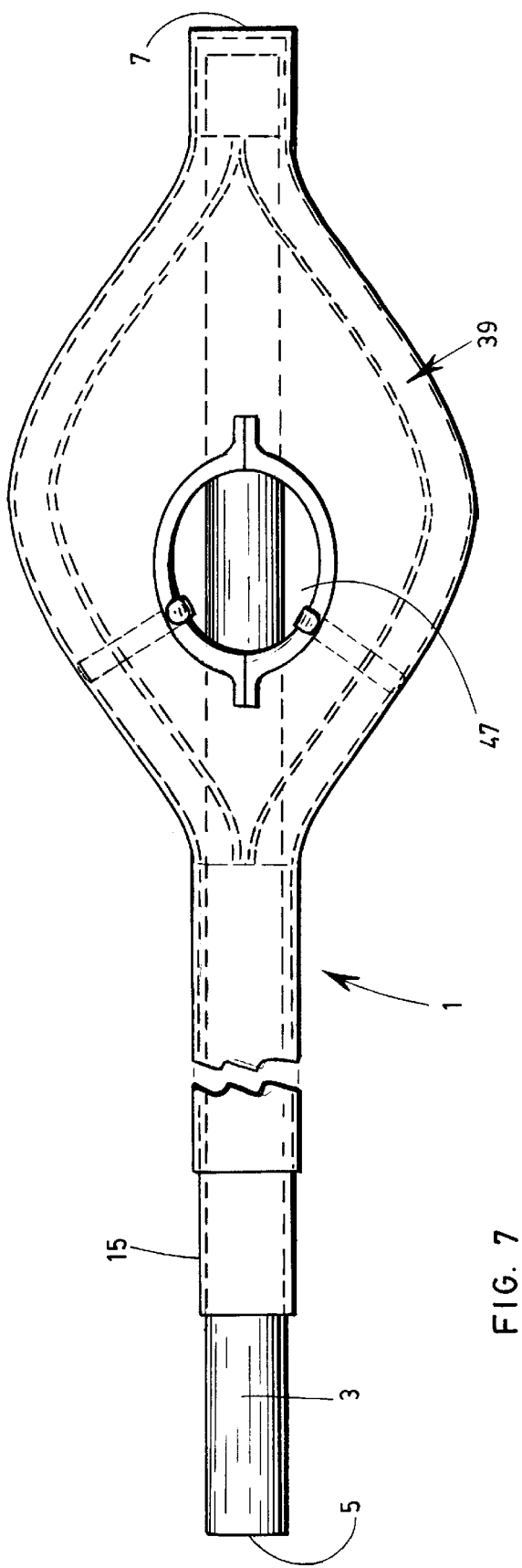

As is shown in FIGS. 6 and 7, a bag 39 hereinafter called "sealing bag" can be mounted on the pusher 15 and the straps 17 in such a manner as to cover at least a radial opening 11 and a second end 7 of the slide 3. The bag 39 is provided with a radial slot 41 which is positioned in such a manner as to extend over the opening. When the pusher 15 is moved in the opening position (see FIG. 7), the straps 17 while they fold up, cause the slot 41 to open and thus allow grasping of the organ that is then inserted within the bag 39. When the pusher is moved to the rest position (see FIG. 6), the bag 39 is retracted together with the straps and such avoids that the organ or crushed parts of it be spread within the body of the patient.

If needs be, the extractor may comprise hooks 43 for connecting the straps 17 which are the closest to the slot 41 directly to the lateral edges of this slot as shown in FIG. 7. This ensures a proper opening of the slot 41 when the pusher 15 is moved in the opening position and a good hermetic closing of the slot 41 when the pusher 15 is moved back in the rest position.

A removable cap 45 (see FIGS. 1 and 2) may also be provided for closing the first open end 5 whenever required.

As may now be better understood, the surgical extractor 1 according to the invention is particularly well adapted for use in laparoscopy. Thanks to its structure, it opens on one side only of its main axis, in the direction D, and thus permits to grasp and catch in the more precise manner the organ to be extracted. Thanks to the means 25, 27 for applying a pressure, the operator may apply a substantial compression force onto the organ to be extracted after it has been grasped so as to crush it, grind it if needs be and thus reduce its size. Moreover, the extractor has the advantage of having an internal tube 3 that is open and thus gives access not only to the extraction zone but also to the organ to be extracted in order to dissect the same and suck it out.

Figure 8:
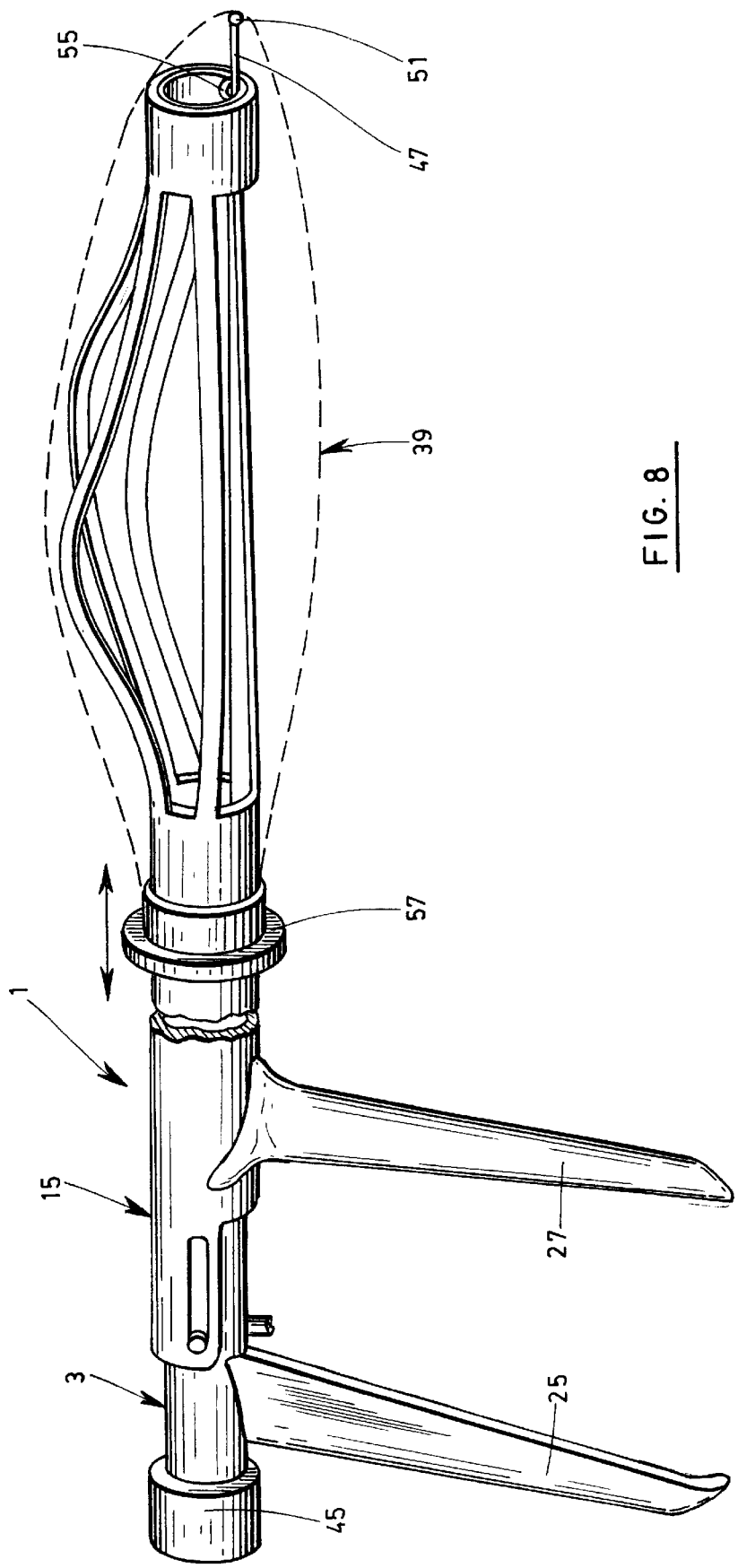
FIG. 8 is a perspective view of a surgical extractor according to a third embodiment of the invention, said extractor being provided with a sealing bag shown in dotted lines.
Figure 9:
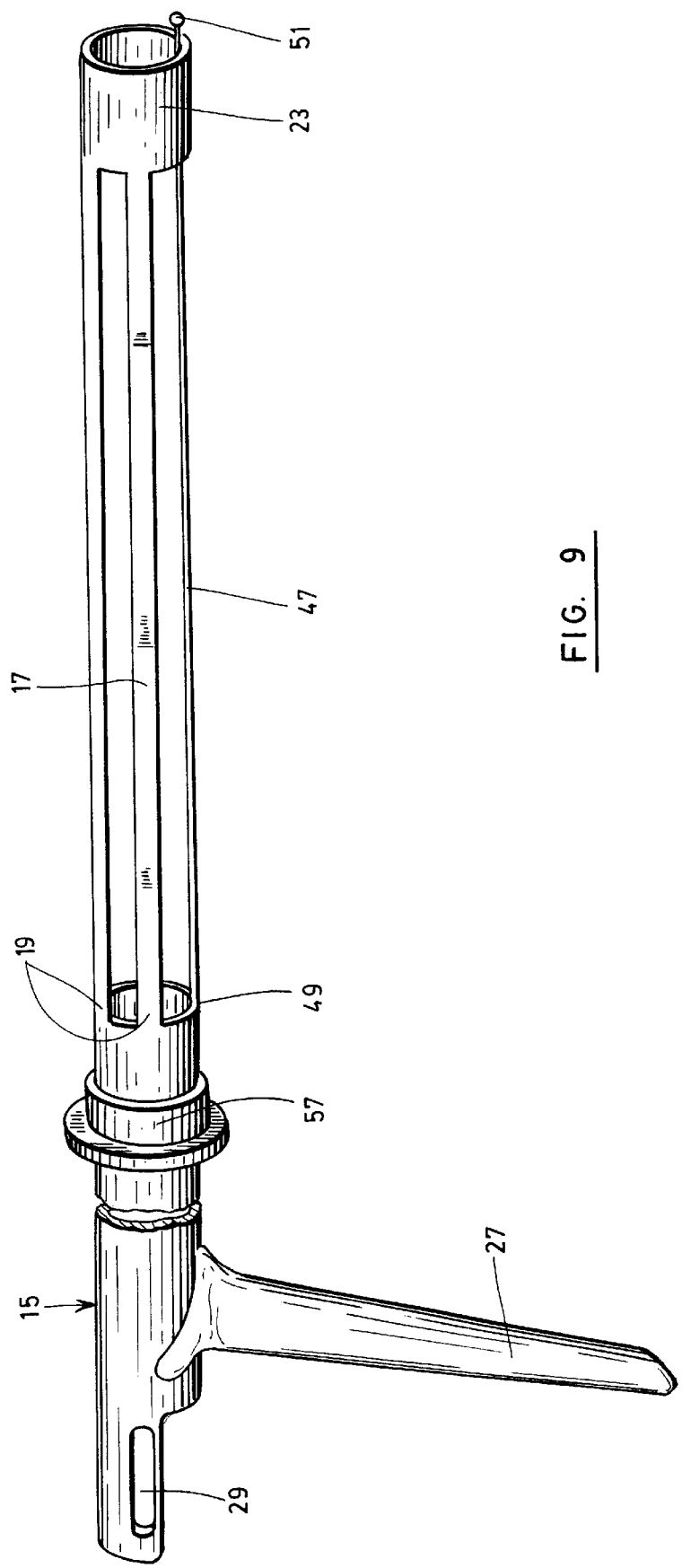
FIG. 9 is a perspective view of the pusher of the extractor as shown in FIG. 8.
Figure 10:
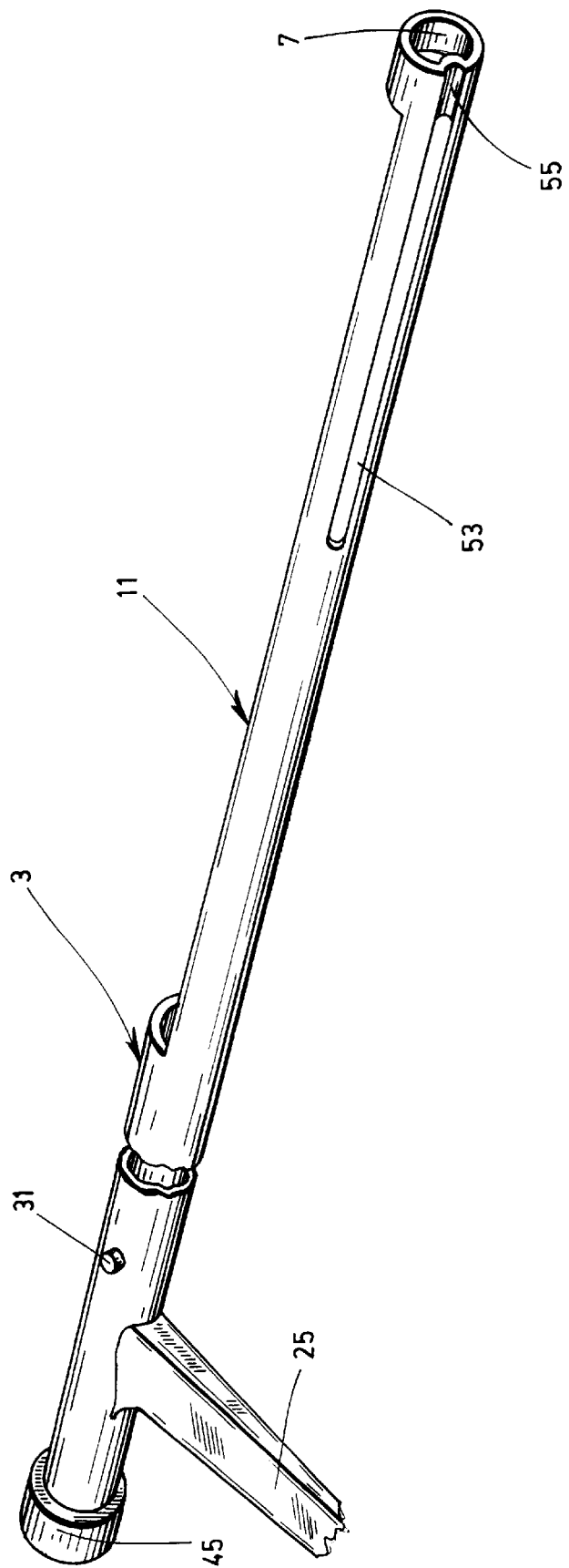
FIG. 10 is a perspective view of the slide of the extractor as shown in FIG. 8.

As is shown in FIGS. 8 to 10, the surgical extractor 1 may be provided with a supplemental strap 47 having a first end 49 fixed in a rigid manner to the pusher 15 under the first ends 19 of the other straps 17, and a second free end 51 with a rounded tip, which passes through the ring 23 retaining the second ends of the other straps. This supplemental strap 47 is devised to be inserted and slide in a longitudinal slot 53 and in a groove 55 provided in the slide 3 under the radial opening 11 and through the second end 7 thereof, respectively.

The addition of this supplemental strap 47 having a free end 51 (also called "distal end") which is free, is mainly used to maintain the distal end of the bag 39 in a proper position during motion of the pusher 15. As shown in FIG. 10, the supplemental strap passes through the groove 55 which defines an opening between the slide and pusher and therefore moves through them without folding.

Another ring 57 may also be mounted in a sliding manner onto the body of the pusher 15. This other ring 57 acts as a fixation support for the bag 39 and thus permits to the operator to pull on the bag or push it away whenever desired (see FIG. 8).

Of course, numerous modifications could be made to the preferred embodiment disclosed hereinabove. Thus, for example, a mechanical system such as a manual lever or an electric or pneumatic piston could be used as an alternative for the means for applying a pressure onto the pusher.

What is claimed is:

1. A surgical extractor comprising:
   a first hollow tube hereinafter called "slide", said slide having a rectilinear longitudinal axis and a constant cross-section, a first open end and a second end, and a long radial opening close to the second end, said radial opening extending over more than half of the section of the slide;
   a second hollow tube hereinafter called "pusher", which is mounted in a sliding manner over the slide;
   several flexible rods hereinafter called "straps", which extend in line with the pusher and each has a first end fixed in a rigid manner to the pusher and a second end connected in a rigid manner to the slide close to the second end of the same, said straps being distributed to extend over the radial opening of the slide; and
   means for applying a pressure onto the pusher comprising handles respectively fixed to the slide and the pusher close to the first open end of said slide so as to:
   in a first step, move the pusher over a given stroke distance from a rest position to an opening position closer to the second end of the slide, such causing the straps to fold up and open like petals over the radial opening and thus to allow grasping in a radial direction of an organ to be extracted from the body of the patient; and
   in a second step, bring the pusher back from its opening position to its rest position while forcing, if needs be, the straps to unfold and thus crush the organ grasped by them, such permitting the organ to pass inside the slide and thus to be extracted from the same through the first open end thereof.

2. The surgical extractor according to claim 1, further comprising:
   a sealing bag mounted onto the slide and straps in order to cover at least the radial opening and the second end of said slide, said bag being provided with the radial slot located above the radial opening to allow insertion within the envelope of the organ grasped by the straps when the slide is in the opening position.

3. A surgical extractor of claim 2, wherein the slot of the sealing bag has lateral edges and said surgical extractor further comprises hooks connecting the straps which are the closest to the slot, to the lateral edges of said slot to ensure proper opening of the slot when the pusher is moved in the opening position, and a good hermetic closing of the slot when the pusher is moved back in the rest position.

4. The surgical extractor according to claim 2, further comprising:
   a supplemental strap having a first end fixed in a rigid manner to the pusher and a second end passing through the second end of the slide, said supplemental strap moving together with the pusher without being folded up when said pusher is moved so as to keep the bag to a given distance.

5. The surgical extractor of claim 2, which further comprises:
   a ring mounted in a sliding manner onto the pusher to maintain the sealing bag.

6. The surgical extractor according to claim 1, wherein the slide comprises a radial outlet close to the first open end for connection thereof to vacuum suction device.

7. The surgical extractor according to claim 1, wherein the second end of the slide is closed.

8. The surgical extractor according to claim 1 for use in laparoscopy, wherein:
   the slide has a length between 40 and 50 cm and a diameter less than 2 cm;
   the radial opening of the slide has a length between 15 and 25 cm; and
   the given stoke distance is between 4 and 8 cm.

9. The surgical extractor according to claim 1, which is made of a biocompatible metal.

10. The surgical extractor according to claim 1, which is made in biocompatible plastic material.

11. A surgical extractor comprising:
- a first hollow tube hereinafter called "slide", said slide having a rectilinear longitudinal axis and a constant cross-section, a first open end and a second end, and a long radial opening close to the second end, said radial opening extending over more than half of the section of the slide;
- a second hollow tube hereinafter called "pusher", which is mounted in a sliding manner over the slide;
- several flexible rods hereinafter called "straps", which extend in line with the pusher and each has a first end fixed in a rigid manner to the pusher and a second end connected in a rigid manner to the slide close to the second end of the same, said straps being distributed to extend over the radial opening of the slide;
- means for applying a pressure onto the pusher so as to:
- in a first step, move the pusher over a given stroke distance from a rest position to an opening position closer to the second end of the slide, such causing the straps to fold up and open like petals over the radial opening and thus to allow grasping in a radial direction of an organ to be extracted from the body of the patient; and
- in a second step, bring the pusher back from its opening position to its rest position while forcing, if needs be, the straps to unfold and thus crush the organ grasped by them, such permitting the organ to pass inside the slide and thus to be extracted from the same through the first open end thereof;
- a bit extending over the full length of the slide within the slide for crushing and extracting the grasped organ; and
- an external motor to rotate the bit.

12. A surgical extractor comprising:
- a first hollow tube hereinafter called "slide", said slide having a rectilinear longitudinal axis and a constant cross-section, a first open end and a second end, and a long radial opening close to the second end, said radial opening extending over more than half of the section of the slide;
- a second hollow tube hereinafter called "pusher", which is mounted in a sliding manner over the slide;
- several flexible rods hereinafter called "straps", which extend in line with the pusher and each has a first end fixed in a rigid manner to the pusher and a second end connected in a rigid manner to the slide close to the second end of the same, said straps being distributed to extend over the radial opening of the slide;
- means for applying a pressure onto the pusher so as to:
- in a first step, move the pusher over a given stroke distance from a rest position to an opening position closer to the second end of the slide, such causing the straps to fold up and open like petals over the radial opening and thus to allow grasping in a radial direction of an organ to be extracted from the body of the patient; and
- in a second step, bring the pusher back from its opening position to its rest position while forcing, if needs be, the straps to unfold and thus crush the organ grasped by them, such permitting the organ to pass inside the slide and thus to be extracted from the same through the first open end thereof;
- wherein the straps form an integral part of the pusher and have their second ends integral to a ring rigidly connected to the second end of the slide.

13. A surgical extractor comprising:
- a first hollow tube hereinafter called "slide", said slide having a rectilinear longitudinal axis and a constant cross-section, a first open end and a second end, and a long radial opening close to the second and, said radial opening extending over more than half of the section of the slide;
- a removable cap for closing the first open end of the slide;
- a second hollow tube hereinafter called "pusher", which is mounted in a sliding manner over the slide;
- several flexible rods hereinafter called "straps", which extend in line with the pusher and each has a first end fixed in a rigid manner to the pusher and a second end connected in a rigid manner to the slide close to the second end of the same, said straps being distributed to extend over the radial opening of the slide;
- means for applying a pressure onto the pusher so as to:
- in a first step, move the pusher over a given stroke distance from a rest position to an opening position closer to the second end of the slide, such causing the straps to fold up and open like petals over the radial opening and thus to allow grasping in a radial direction of an organ to be extracted from the body or the patient; and
- in a second step, bring the pusher back from its opening position to its rest position while forcing, if needs be, the straps to unfold and thus crush the organ grasped by them, such permitting the organ to pass inside the slide and thus to be extracted from the same through the first open end thereof.

14. A surgical extractor comprising:
- a first hollow tube hereinafter called "slide", said slide having a rectilinear longitudinal axis and a constant cross-section, a first open end and a second closed end, a radial outlet close to the first open end for connection thereof to a vacuum suction device, and a long radial opening close to the second end, said radial opening extending over more than half of the section of the slide and having a length between 15 and 25 cm, said slide having a length between 40 and 50 cm and a diameter less than 2 cm;
- a second hollow tube hereinafter called "pusher", which is mounted in a sliding manner over the slide;
- several flexible rods hereinafter called "straps", which extend in line with the pusher and each has a first end fixed in a rigid manner to the pusher and a second end connected in a rigid manner to the slide close to the second end of the same, said straps being distributed to extend over the radial opening of the slide;
- means for applying a pressure onto the pusher so as to:
- in a first step, move the pusher over a given stroke distance between 4 and 8 cm from a rest position to an opening position closer to the second end of the slide, such causing the straps to fold up and open like petals over the radial opening and thus to allow grasping in a radial direction of an organ to be extracted from the body of the patient; and
- in a second step, bring the pusher back from its opening position to its rest position while forcing, if needs be, the straps to unfold and thus crush the organ grasped by them, such permitting the organ to pass inside the slide and thus to be extracted from the same through the first open end thereof.

* * * * *